United States Patent
Li et al.

(10) Patent No.: US 11,899,005 B2
(45) Date of Patent: Feb. 13, 2024

(54) DIVISIBLE EXPERIMENTAL DEVICE AND METHOD FOR SAND PRODUCTION AND SAND CONTROL DURING NATURAL GAS HYDRATE EXPLOITATION

(71) Applicant: GUANGZHOU INSTITUTE OF ENERGY CONVERSION, CHINESE ACADEMY OF SCIENCES, Guangzhou (CN)

(72) Inventors: Xiaosen Li, Guangzhou (CN); Yi Wang, Guangzhou (CN); Zhaoyang Chen, Guangzhou (CN); Zhiming Xia, Guangzhou (CN); Gang Li, Guangzhou (CN); Yu Zhang, Guangzhou (CN)

(73) Assignee: GUANGZHOU INSTITUTE OF ENERGY CONVERSION, CHINESE ACADEMY OF SCIENCES, Guangzhou (CN)

( * ) Notice: Subject to any disclaimer, the term of this patent is extended or adjusted under 35 U.S.C. 154(b) by 260 days.

(21) Appl. No.: 17/257,311

(22) PCT Filed: Sep. 8, 2020

(86) PCT No.: PCT/CN2020/114106
§ 371 (c)(1),
(2) Date: Dec. 29, 2021

(87) PCT Pub. No.: WO2021/159701
PCT Pub. Date: Aug. 19, 2021

(65) Prior Publication Data
US 2022/0299495 A1    Sep. 22, 2022

(30) Foreign Application Priority Data
Aug. 7, 2020  (CN) .......................... 202010789778.0

(51) Int. Cl.
*G01N 33/24* (2006.01)
*B01J 19/18* (2006.01)
(Continued)

(52) U.S. Cl.
CPC .......... *G01N 33/24* (2013.01); *B01J 19/1818* (2013.01); *B01J 2219/00094* (2013.01);
(Continued)

(58) Field of Classification Search
None
See application file for complete search history.

(56) References Cited

U.S. PATENT DOCUMENTS 9,970,267 B2 * 5/2018 Li ........................ G01N 33/241
10,095,819 B2 * 10/2018 Li ............................. E21B 7/00
(Continued)

FOREIGN PATENT DOCUMENTS

CN          205786187 U  * 12/2016
CN          206008676 U     3/2017
(Continued)

OTHER PUBLICATIONS

"Experimental Investigation of Characteristics of Sand Production in Wellbore during Hydrate Exploitation by the Depressurization Method"—energies; Lu et al.; Jun. 27, 2018; pp. 1-17 (Year: 2018).*
"Experimental study of sand control in a natural gas hydrate reservoir in the South China Sea"—International Journal of Hydrogen Energy; Ding et al.; Sep. 3, 2019; pp. 1-16 (Year: 2019).*

*Primary Examiner* — Ryan D Walsh
(74) *Attorney, Agent, or Firm* — Bayramoglu Law Offices LLC

(57) ABSTRACT

A divisible device and a method for sand production and sand control experiment for natural gas hydrate exploitation. The experimental device includes a reactor system, a feeding system, a separation and measurement system, a water-bath jacket system, a support and safety system, and a software
(Continued)

recording and analyzing system. In the reactor system, the reactor units can be combined in different ways depending on the experimental conditions and purposes. The reactor units include: left/right reactor units, secondary reactor units, central reactor units, and caps. The combination of a left/right reactor unit with a cap gives a hydrate formation reactor without sand control screens. Combining the left/right reactor unit, secondary left/right reactor units and central reactor units with other accessories allows the reactor system to carry out the simulation experiments with either zero, one, or two view zones, and with either one or two wells.

20 Claims, 15 Drawing Sheets

(51) Int. Cl.
   *E21B 43/08* (2006.01)
   *E21B 41/00* (2006.01)

(52) U.S. Cl.
   CPC ............... *B01J 2219/00283* (2013.01); *B01J 2219/00286* (2013.01); *B01J 2219/00337* (2013.01); *B01J 2219/00423* (2013.01); *E21B 41/0099* (2020.05); *E21B 43/084* (2013.01); *E21B 2200/20* (2020.05)

(56) References Cited

U.S. PATENT DOCUMENTS

| | | | |
|---|---|---|---|
| 10,683,736 B2* | 6/2020 | Chen | ............... E21B 43/168 |
| 11,708,748 B2* | 7/2023 | Li | ............... E21B 43/35 |
| | | | 166/250.01 |
| 2004/0084186 A1 | 5/2004 | Allison | |

FOREIGN PATENT DOCUMENTS

| | | | | | |
|---|---|---|---|---|---|
| CN | 107045054 | A | 8/2017 | | |
| CN | 107462677 | A | 12/2017 | | |
| CN | 107478809 | A | 12/2017 | | |
| CN | 109025985 | A | 12/2018 | | |
| CN | 109696360 | A | 4/2019 | | |
| CN | 208990766 | U | 6/2019 | | |
| CN | 110346529 | A | 10/2019 | | |
| CN | 110454146 | A | 11/2019 | | |
| CN | 110630228 | A | 12/2019 | | |
| CN | 111259564 | A | 6/2020 | | |
| CN | 210858697 | U | 6/2020 | | |
| CN | 111396001 | A | 7/2020 | | |
| CN | 111411943 | A | 7/2020 | | |
| CN | 111999466 | A | * 11/2020 | ........... | G01N 33/222 |
| FR | 2687223 | A1 | 8/1993 | | |
| JP | 3224246 | U | 12/2019 | | |
| KR | 101621504 | B1 | 5/2016 | | |

* cited by examiner

DIVISIBLE EXPERIMENTAL DEVICE AND METHOD FOR SAND PRODUCTION AND SAND CONTROL DURING NATURAL GAS HYDRATE EXPLOITATION

CROSS REFERENCE TO THE RELATED APPLICATIONS

This application is the national phase entry of International Application No. PCT/CN2020/114106, filed on Sep. 8, 2020, which is based upon and claims priority to Chinese Patent Application No. 202010789778.0, filed on Aug. 7, 2020, the entire contents of which are incorporated herein by reference.

TECHNICAL FIELD

The present invention relates to the sand production and sand control experiment for natural gas hydrate exploitation, and particularly relates to a divisible device and a method for sand production and sand control experiment for natural gas hydrate exploitation.

BACKGROUND

With the increasing depletion of traditional energy sources, natural gas hydrates, featured by large reserves, high energy density and wide distribution, have become a alternative energy source with great potential. Currently, as global study and development on natural gas hydrates are turning to exploitation practices, people are being faced with a severe problem—sand blockage, which has become a key issue that restricts the long-term sustainable exploitation of natural gas hydrates. Accordingly, studying sand production and sand control during the exploitation of natural gas hydrates is of great significance.

Existing simulation devices lack flexibility as they only allow simulation of sand production and sand control of very few situations. As existing devices are not modularized but complicate in structure, it is difficult to design multiple experimental protocols with one device.

SUMMARY

In view of the deficiency in prior art, the present invention provides a divisible device and a method for sand production and sand control experiment for natural gas hydrate exploitation. The reactor system of the device is featured by its flexible assembling design, wherein the components of the system can be assembled in different combinations for studying sand production and sand control for various purposes. In order to realize the above object, the present invention comprises the following technical solutions.

One aspect is a divisible device for simulation experiments of sand production and sand control in natural gas hydrate exploitation, comprising a reactor system and a feeding system, wherein, it further comprises a separation and measurement system, a water-bath jacket system, a support and safety system, and a software recording and analyzing system;

the feeding system is configured to introduce gas, liquid, and sands into the reactor system to allow formation of natural gas hydrates in the reactor system;

the reactor system is disposed in the water-bath jacket system, and the water-bath jacket system is configured to regulate a temperature inside the reactor system for simulating an ambient temperature of a natural gas hydrate reservoir;

the support and safety system comprises a base, wherein the water-bath jacket system is vertically or horizontally fixable on the base for simulating the sand production and sand control by sand control screens at various positions in the natural gas hydrate reservoir;

the base is provided with a data collecting module, wherein the data collecting module collects data from the reactor system during a simulated exploitation by a plurality of sensors;

the separation and measurement system is connected to a production outlet of the reactor system for simulating a inflow of a gas-liquid-sand mixture during the simulated exploitation; the separation and measurement system is configured to separate and measure the gas-liquid-sand mixture, and send measurement data to the data collecting module;

the software recording and analyzing system is communicatingly connected with the data collecting module;

the reactor system comprises first reactor units, second reactor units, third reactor units, ball valves, meshes, and caps; the first reactor units each comprises a cylindrical casing with a first end being open and a second end being closed; the second reactor units and the third reactor units each comprises a cylindrical casing with both ends being open; the cylindrical casing of each of the first reactor units, the second reactor units, and the third reactor units is provided with holes for disposing sensors; the first reactor units, the second reactor units, and the third reactor units are each provided with a pressure relief opening and a liquid discharging opening; the first reactor units and the third reactor units are each further provided with a sand inlet, a water inlet, a methane inlet, a production outlet, and a sight opening; the caps are each provided with a production outlet; and combining the first reactor units, the second reactor units, the third reactor units, the ball valves, the meshes, and the caps in a plurality of ways allows the reactor system to carry out the simulation experiments with either zero, one, or two view zones, with either one or two wells, and with sand control screens being disposed at various positions in the natural gas hydrate reservoir.

Furthermore, the first reactor units and the third reactor units are further provided with moveable pistons, the second end of each of the first reactor units and the cylindrical casing of each of the third reactor units is provided with a nitrogen inlet configured to introduce nitrogen gas to drive the moveable pistons move toward the ends where materials are fed, wherein, each of the first reactor units is provided with one movable piston that is movable toward the first end of the first reactor unit during operation, and each of the third reactor units is provided with two movable pistons that are each moveable toward either end of the third reactor unit during operation.

Furthermore, the reactor system is configured to carry out the simulation experiment with no view zone and one well, by assembling in an order of first reactor unit, ball valve, mesh, second reactor unit, mesh, and cap, wherein the first reactor unit is configured to simulate a hydrate zone, the combination of ball valve, mesh, second reactor unit, and mesh is configured to simulate a sand control screen zone, and the cap is configured to simulate a sand production outlet; the reactor system being vertically assembled with the cap being disposed at bottom allows to carry out the simulation experiment with the sand control screens being disposed below the natural gas hydrate reservoir; the reactor system being horizontally assembled allows to carry out the simulation experiment with the sand control screens being disposed laterally to the natural gas hydrate reservoir; the reactor system being vertically assembled with the cap being disposed at top allows to carry out the simulation experiment with the sand control screens being disposed above the natural gas hydrate reservoir.

Furthermore, the reactor system is configured to carry out the simulation experiment with no view zone and two wells, by assembling in an order of cap, mesh, second reactor unit, mesh, ball valve, third reactor unit, ball valve, mesh, second reactor unit, mesh, and cap, wherein the third reactor unit is configured to simulate a hydrate zone, each combination of ball valve, mesh, second reactor unit, and mesh is configured to simulate a sand control screen zone, and each cap is configured to simulate a sand production outlet; the reactor system being vertically assembled allows to carry out the simulation experiment with the sand control screens being disposed above and below the natural gas hydrate reservoir; the reactor system being horizontally assembled allows to carry out the simulation experiment with the sand control screens being disposed laterally to the natural gas hydrate reservoir.

Furthermore, the reactor system is configured to carry out the simulation experiment with one view zone and one well, by assembling in an order of first reactor unit, ball valve, mesh, second reactor unit, mesh, and first reactor unit, wherein the first reactor unit close to the ball valve is configured to simulate a hydrate zone, the combination of ball valve, mesh, second reactor unit, and mesh is configured to simulate a sand control screen zone, and the first reactor unit far away from the ball valve is configured to simulate the view zone and a sand production outlet; the reactor system being vertically assembled with the ball valve being disposed at an upper side allows to carry out the simulation experiment with the sand control screens being disposed below the natural gas hydrate reservoir, wherein, the first reactor unit far away from the ball valve is equivalent to a combination of one third reactor unit and one cap; the reactor system being vertically assembled with the ball valve being disposed at a lower side allows to carry out the simulation experiment with the sand control screens being disposed above the natural gas hydrate reservoir; the reactor system being horizontally assembled allows to carry out the simulation experiment with the sand control screens being disposed laterally to the natural gas hydrate reservoir.

Furthermore, the reactor system is configured to carry out the simulation experiment with one view zone and two wells, by assembling in an order of first reactor unit, ball valve, mesh, second reactor unit, mesh, third reactor unit, mesh, second reactor unit, mesh, ball valve, and cap, wherein:

the reactor system being horizontally assembled in an order of first reactor unit, ball valve, mesh, second reactor unit, mesh, third reactor unit, mesh, second reactor unit, mesh, ball valve, and cap allows to carry out the simulation experiment with the sand control screens being disposed laterally to the natural gas hydrate reservoir, wherein, the first reactor unit is configured to simulate a hydrate zone, the combination of ball valve, mesh, second reactor unit, and mesh is configured to simulate a sand control screen zone; the third reactor unit is configured to simulate the view zone and a sand production outlet, the combination of mesh, second reactor unit, mesh, and ball valve is configured to simulate another sand control screen zone, and the cap is configured to simulate another sand production outlet; or the reactor system being vertically assembled in an order of first reactor unit, ball valve, mesh, second reactor unit, mesh, third reactor unit, mesh, second reactor unit, mesh, ball valve, and cap allows to carry out the simulation experiment with the sand control screens being disposed below the natural gas hydrate reservoir, wherein, the first reactor unit is configured to simulate a hydrate zone, the combination of ball valve, mesh, second reactor unit, and mesh is configured to simulate a sand control screen zone, the third reactor unit is configured to simulate the view zone and a sand production outlet, the combination of mesh, second reactor unit, mesh, and ball valve is configured to simulate another sand control screen zone, and the cap is configured to simulate another sand production outlet; or the reactor system being vertically assembled in an order of first reactor unit, mesh, second reactor unit, mesh, ball valve, third reactor unit, ball valve, mesh, second reactor unit, mesh, and cap allows to carry out the simulation experiment with the sand control screens being disposed above and below the natural gas hydrate reservoir, wherein, the first reactor unit is configured to simulate the view zone and a sand production outlet, the combination of mesh, second reactor unit, mesh, and ball valve is configured to simulate a sand control screen zone, and the third reactor unit is configured to simulate a hydrate zone.

Furthermore, the reactor system is configured to carry out the simulation experiment with two view zones and one well, by assembling in an order of first reactor unit, mesh, second reactor unit, mesh, ball valve, third reactor unit, ball valve, mesh, second reactor unit, mesh, and cap, wherein, the first reactor unit is configured to simulate a hydrate zone, each combination of mesh, second reactor unit, mesh, and ball valve is configured to simulate a sand control screen zone, and the third reactor unit is configured to simulate the view zones and a sand production outlet; the reactor system being horizontally assembled allows to carry out the simulation experiment with two natural gas hydrate reservoirs being disposed on both sides of the sand control screens; the reactor system being vertically assembled allows to carry out the simulation experiment with two natural gas hydrate reservoirs being disposed both above and below the sand control screens.

Furthermore, the reactor system is configured to carry out the simulation experiment with two view zones and two wells, by assembling in an order of first reactor unit, mesh, second reactor unit, mesh, ball valve, third reactor unit, ball valve, mesh, second reactor unit, mesh, and cap, wherein:

the reactor system being horizontally or vertically assembled in an order of first reactor unit, mesh, second reactor unit, mesh, ball valve, third reactor unit, ball valve, mesh, second reactor unit, mesh, and cap allows to carry out the simulation experiment with the sand control screens being disposed at both sides of the natural gas hydrate reservoir, wherein, the third reactor unit is configured to simulate a hydrate zone, each combination of mesh, second reactor unit, mesh, and ball valve is configured to simulate a sand control screen zone, the first reactor unit is configured to simulate one view zone, and the cap is configured to simulate a sand production outlet; or the reactor system being horizontally assembled in an order of first reactor unit, ball valve, mesh, second reactor unit, mesh, third reactor unit, mesh, second reactor unit, mesh, ball valve, and cap allows to carry out the simulation experiment with the sand control screens being disposed laterally to the natural gas hydrate reservoir and with directions of sand production in the two wells being identical to each other, wherein, the first reactor unit is configured to simulate a hydrate zone, each combination of ball valve, mesh, second reactor unit, mesh is configured to simulate a sand control screen zone, the third reactor unit is configured to simulate one view zone and a sand production outlet, and the first reactor unit is configured to simulate another view zone and another sand production outlet; or the reactor system being vertically assembled in an order of first reactor unit, ball valve, mesh, second reactor unit, mesh, third reactor unit, mesh, second reactor unit, mesh, ball valve, and cap from bottom to up allows to carry out the simulation experiment with the sand control screens being disposed above the natural gas hydrate reservoir and with directions of sand production in the two wells being identical to each other, wherein, the first reactor unit is configured to simulate a hydrate zone, each combination of ball valve, mesh, second reactor unit, mesh is configured to simulate a sand control screen zone, the third reactor unit is configured to simulate one view zone and a sand production outlet, and the first reactor unit is configured to simulate another view zone and another sand production outlet; or the reactor system being vertically assembled in an order of first reactor unit, ball valve, mesh, second reactor unit, mesh, third reactor unit, mesh, second reactor unit, mesh, ball valve, and cap from up to bottom allows to carry out the simulation experiment with the sand control screens being disposed below the natural gas hydrate reservoir and directions of sand production in the two wells being identical to each other, wherein, the first reactor unit is configured to simulate a hydrate zone, each combination of ball valve, mesh, second reactor unit, mesh is configured to simulate a sand control screen zone, the third reactor unit is configured to simulate one view zone and a sand production outlet, and the first reactor unit is configured to simulate another view zone and another sand production outlet; or the reactor system being horizontally or vertically assembled in an order of first reactor unit, ball valve, mesh, second reactor unit, mesh, third reactor unit, mesh, second reactor unit, mesh, ball valve, and cap allows to carry out the simulation experiment with two natural gas hydrate reservoirs being disposed on both sides of the sand control screens and directions of sand production in the two wells being opposite to each other, wherein, the first reactor unit is configured to simulate a hydrate zone, each combination of ball valve, mesh, second reactor unit, mesh is configured to simulate a sand control screen zone, and the third reactor unit is configured to simulate one view zone and a sand production outlet.

Any one device as described above is further characterized in that, the caps are hemispherical caps when the reactor system is vertically assembled or flat caps when the reactor system is horizontally assembled, and a combination of one third reactor unit and one cap is equivalent to one first reactor unit.

Furthermore, the sight opening comprises an upper sight glass and a lower sight glass configured to allow real-time inspection on the sand production and changes inside each unit of the reactor system.

Furthermore, the feeding system comprises a nitrogen gas supply, a water supply, a screen material supply, a reservoir material supply, and a methane gas supply; the nitrogen gas supply is connected with the nitrogen inlet of the reactor system, through a nitrogen gas pipeline provided with a nitrogen gas flow meter, a nitrogen gas pressure gauge, and a nitrogen gas valve; the water supply is connected to the water inlet of the reactor system, through a water pipeline provided with a water flow meter, a water pressure gauge, and a water valve; the screen material supply is connected to the sand inlet of the reactor system, through a screen sand pipeline provided with a screen material-weighing device and a screen sand barrier; the reservoir material supply is connected to the sand inlet of the reactor system, through a reservoir sand pipeline provided with a reservoir material-weighing device and a reservoir sand barrier; the screen sand barrier and the reservoir sand barrier are configured to enable sealing of the sand inlet; the methane gas supply is connected to the methane inlet, through a methane gas pipeline provided with a methane gas flow meter, a methane gas pressure gauge, and a methane gas valve; the nitrogen gas pipeline, the water pipeline, the screen sand pipeline, the reservoir sand pipeline, and the methane gas pipeline are each connected to a data collector through a data cable, wherein the data collector is configured to collect data in real time.

Furthermore, the separation and measurement system comprises sand-measuring cylinders, a water-measuring cylinder, and a filter passage; the filter passage comprises a first sand screen, a second sand screen, and a third sand screen, with successively reduced pore sizes (i.e., a coarse sand screen, an intermediate sand screen, and a fine sand screen; the pore sizes may be determined depending on actual needs); an inlet of the filter passage is connected to the production outlet of the reactor system and provided with a reducing valve, and an outlet of the filter passage is connected to an inlet of the water-measuring cylinder; an outlet of the water-measuring cylinder is connected to an inlet of a gas-collecting tank, through a pipeline provided with a cylinder outlet flow meter and a cylinder outlet pressure gauge; the sand-measuring cylinders are respectively disposed downstream of the coarse sand screen, the intermediate sand screen, and the fine sand screen; an unscrewable threaded cap is provided at a bottom of each of the sand-measuring cylinders and the water-measuring cylinder. The separation and measurement system may further comprise a camera, wherein the camera is configured to record a process of separating the gas-liquid-sand mixture. The separation and measurement system may further comprise a data collector for collecting data from the camera, the reducing valve, the cylinder outlet flow meter and the cylinder outlet pressure gauge.

Furthermore, the water-bath jacket system comprises a thermostat and a jacket casing; the jacket casing comprises a temperature-controlling water outlet and a temperature-controlling water inlet; the temperature-controlling water outlet and the temperature-controlling water inlet are each connected to the thermostat through a hose, wherein the thermostat is configured to regulate a temperature of water inflowing from the temperature-controlling water outlet and send the water to the temperature-controlling water inlet; the jacket casing is provided with passages mating with the holes or openings of the reactor system.

Furthermore, the reactor system is provided with supporting nuts, the water jacket is provided with fixing nuts, and the base is provided with horizontal fixing rods and vertical fixing rods; the horizontal fixing rods and the vertical fixing rods are each provided with fixing holes; the reactor system and the water-bath jacket system are vertically or horizontally fixable on the base by using fixing units to connect the supporting nuts/fixing nuts to the fixing holes.

The coordination of the systems comprises: the reactor system is disposed in the water-bath jacket system, while the water-bath jacket system is disposed on the support and safety system; the feeding system provides gas, water, and sands to the reactor system, and then the reactor system gives a gas-liquid-sand mixture to the separation and measurement system; data collection and power supply of the whole device are realized by the support and safety system, wherein the data collector therein sends the data to the software recording and analyzing system for inspecting, processing, and analyzing the data.

Depending on the experimental conditions and purposes, the reactor system can be assembled in different combinations. The combination of a left/right reactor unit (the first reactor unit) with a cap gives a hydrate formation reactor without sand control screens. Combining the left/right reactor unit, secondary left/right reactor units (the second reactor units) and central reactor units (the third reactor unit) with other accessories allows the reactor system to carry out the simulation experiments with either zero, one, or two view zones, and with either one or two wells. A left/right reactor unit or a central reactor unit can serve as a hydrate zone or view zone, and a secondary left/right reactor unit with a mesh provided at each end can serve as a sand control screen zone.

For simulation experiments with no view zone and one well, three combinations are useful. In the first combination, the reactor system is vertically assembled in an order (from top to bottom) of a hydrate zone (a left reactor unit), a sand control screen zone (a secondary reactor unit), and a sand production outlet (a hemispherical cap), to carry out the simulation experiments with the sand control screens being disposed below the natural gas hydrate reservoir. In the second combination, the reactor system is horizontally assembled in an order (from left to right) of a hydrate zone (a left reactor unit), a sand control screen zone (a secondary reactor unit), and a sand production outlet (a flat cap), to carry out the simulation experiments with the sand control screens being disposed on the right side of the natural gas hydrate reservoir. In the third combination, the reactor system is vertically assembled in an order (from bottom to top) of a hydrate zone (a left reactor unit), a sand control screen zone (a secondary reactor unit), and a sand production outlet (a flat cap), to carry out the simulation experiments with the sand control screens being disposed above the natural gas hydrate reservoir.

For simulation experiments with no view zone and two wells, two combinations are useful. In the first combination, the reactor system is vertically assembled in an order (from top to bottom) of a sand production outlet (a flat cap), a sand control screen zone (a secondary reactor unit), a hydrate zone (a central reactor unit), a sand control screen zone (a secondary reactor unit), and a sand production outlet (a hemispherical cap), to carry out the simulation experiments with the sand control screens being disposed above and below the natural gas hydrate reservoir. In the second combination, the reactor system is horizontally assembled in an order (from left to right) of a sand production outlet (a flat cap), a sand control screen zone (a secondary reactor unit), a hydrate zone (a central reactor unit), a sand control screen zone (a secondary reactor unit), and a sand production outlet (a flat cap), to carry out the simulation experiments with the sand control screens being disposed on both left and right sides of the natural gas hydrate reservoir. Whether a piston is required in the hydrate zone depends on actual demand; when it is necessary to compact the reservoir material in the reactor, the piston is disposed inside for compacting the reservoir material; if the reservoir material is compacted before placed into the central reactor unit through the opening of two ends, the piston is not required.

For simulation experiments with one view zone and one well, four combinations are useful. In the first combination, the reactor system is vertically assembled in an order (from top to bottom) of a hydrate zone (a left reactor unit), a sand control screen zone (a secondary reactor unit), a view zone (a second left reactor unit), and a sand production outlet (a production outlet of the second left reactor unit), to carry out the simulation experiments with the sand control screens being disposed below the natural gas hydrate reservoir. In the second combination, the reactor system is vertically assembled in an order (from bottom to top) of a hydrate zone (a left reactor unit), a sand control screen zone (a secondary reactor unit), a view zone (a second left reactor unit), and a sand production outlet (a production outlet of the second left reactor unit), to carry out the simulation experiments with the sand control screens being disposed above the natural gas hydrate reservoir. In the third combination, the reactor system is horizontally assembled in an order (from left to right) of a hydrate zone (a left reactor unit), a sand control screen zone (a secondary reactor unit), a view zone (a second left reactor unit), and a sand production outlet (a production outlet of the second left reactor unit), to carry out the simulation experiments with the sand control screens being disposed on the right side of the natural gas hydrate reservoir. In the fourth combination, the reactor system is vertically assembled in an order (from top to bottom) of a hydrate zone (a left reactor unit), a sand control screen zone (a secondary reactor unit), a view zone (a second left reactor unit), and a sand production outlet (a hemispherical cap), to carry out the simulation experiments with the sand control screens being disposed below the natural gas hydrate reservoir.

For simulation experiments with one view zone and two wells, three combinations are useful. In the first combination, the reactor system is horizontally assembled in an order (from left to right) of a hydrate zone (a left reactor unit), a sand control screen zone (a secondary reactor unit), a view zone (a central reactor unit also comprising a sand production outlet), a sand control screen zone (another secondary reactor unit), and a sand production outlet (a flat cap), to carry out the simulation experiments with the sand control screens being disposed on the right side of the natural gas hydrate reservoir. In the second combination, the reactor system is vertically assembled in an order (from top to bottom) of a sand production outlet (a production outlet of a left reactor unit), a view zone (a left reactor unit), a sand control screen zone (a secondary reactor unit), a hydrate zone (a central reactor unit), a sand control screen zone (a secondary reactor unit), and a sand production outlet (a hemispherical cap), to carry out the simulation experiments with the sand control screens being disposed both above and below the natural gas hydrate reservoir. In the third combination, the reactor system is vertically assembled in an order (from top to bottom) of a hydrate zone (a left reactor unit), a sand control screen zone (a secondary reactor unit), a view zone (a central reactor unit also comprising a sand production outlet), a sand control screen zone (another secondary reactor unit), and a sand production outlet (a hemispherical cap), to carry out the simulation experiments with the sand control screens being disposed below the natural gas hydrate reservoir. The two sand control screen zones and the two sand production outlets are for simulation of sand production via two screen sections.

For simulation experiments with two view zones and one well, two combinations are useful. In the first combination, the reactor system is horizontally assembled in an order (from left to right) of a hydrate zone (a left reactor unit), a sand control screen zone (a secondary reactor unit), a sand production outlet (a left production outlet of a central reactor unit), a view zone (the central reactor unit), a sand production outlet (a right production outlet of the central reactor unit), a sand control screen zone (a secondary reactor unit), and a hydrate zone (a left reactor unit), to carry out the simulation experiments with two natural gas hydrate reservoirs being disposed on both sides of the sand control screens. In the second combination, the reactor system is horizontally assembled in an order (from top to bottom) of a hydrate zone (a left reactor unit), a sand control screen zone (a secondary reactor unit), a sand production outlet (a left production outlet of a central reactor unit), a view zone (the central reactor unit), a sand production outlet (a right production outlet of the central reactor unit), a sand control screen zone (a secondary reactor unit), and a hydrate zone (a left reactor unit), to carry out the simulation experiments with two natural gas hydrate reservoirs being disposed both above and below the sand control screens. The two combinations provide excellent simulation of sand production in vertical wells and horizontal wells during actual exploitation of hydrates.

For simulation experiments with two view zones and two wells, seven combinations are useful. In the first and second combinations, the reactor system is respectively horizontally and vertically assembled in an order (from center to each end) of a hydrate zone (a central reactor unit), a sand control screen zone (a secondary reactor unit), a view zone (a left/right reactor unit), and a sand production outlet (a production outlet of the left/right reactor unit or a hemispherical cap) to carry out the simulation experiments with the sand control screens being disposed above and below (or on both sides of) the natural gas hydrate reservoir, with directions of sand production in the two wells being opposite to each other; whether pistons are required depends on whether the reservoir material is compacted. In the third, fourth, and fifth combinations, the reactor system is respectively horizontally, vertically, and vertically assembled in an order (respectively from left, bottom, and top to the corresponding other end) of a hydrate zone (a left reactor unit), a sand control screen zone (a secondary reactor unit), a view zone (a central reactor unit), a sand production outlet (a production outlet of the central reactor unit), a sand control screen zone (a secondary reactor unit), a view zone (a left reactor unit), a sand production outlet (a production outlet of the left reactor unit), to carry out the simulation experiments with the sand control screens being disposed one the right side of, above, or below the natural gas hydrate reservoir, with directions of sand production in the two wells being identical to each other. In the sixth and seven combinations, the reactor system is respectively horizontally and vertically assembled in an order (from each end to center) of a hydrate zone (a left reactor unit), a sand control screen zone (a secondary reactor unit), a view zone (a central reactor unit), and a sand production outlet (a left/right production outlet of the central reactor unit), to carry out the simulation experiments with two natural gas hydrate reservoirs being disposed on both sides of (or both above and below) the sand control screens, with directions of sand production in the two wells being opposite to each other.

Another aspect is a method for simulation experiment of sand production and sand control in natural gas hydrate exploitation using any one device as described above, comprising the following steps:

assembling the reactor system to give a combination according to a purpose of the simulation experiment, placing a reservoir material partially in a corresponding reactor unit according to the combination, disposing sensors in the corresponding holes, wherein the sensors include pressure sensors, temperature sensors, and resistance sensors;

connecting the feeding system and the separation and measurement system to the corresponding inlets or outlets of the reactor system, vertically or horizontally disposing the reactor system in the water-bath jacket system, and fixing the in the water-bath jacket system on the base;

performing an air tightness test on the reactor system and the water-bath jacket system;

filling the corresponding reactor unit with the reservoir material, introducing water and methane gas into the reactor system to a predetermined pressure according to the simulation experiments to initiate formation of natural gas hydrates under the predetermined pressure and the temperature regulated by the water-bath jacket system; monitoring a pressure change in the reactor system via the pressure sensors, wherein the formation of natural gas hydrates is complete when the pressure change in a specific period is zero or below a predetermined value;

performing the simulated exploitation via the depressurization method or the thermal stimulation method, and separating and measuring the gas-liquid-sand mixture via the separation and measurement system;

when a pressure of produced gas reduces to a predetermined value and stops changing, terminating the simulated exploitation, and sending the measurement data to the software recording and analyzing system via the support and safety system.

Compared with prior art, the beneficial effect of the present invention lies in that, the whole device can be assembled in different combinations according to different simulation experiments, allowing studies on multiphase flow, simulation and measurement of sand production, and optimization of sand control schemes.

The units of the reactor system can be combined according to the experimental purpose. Particularly, the reactor system comprises reactor units of three different types (the left/right reactor units, the secondary reactor units, and the central reactor units) and other accessories. The three different types of reactor units can be connected through flange connection. The left/right reactor units and the central reactor units can realize the observation and measurement of sand production, the filling of materials, the simulated exploitation of gas-liquid-sand mixture, and the feeding of gas and water for the formation of natural gas hydrates. The secondary reactor units can realize the observation, filling of sands, the simulated exploitation, and the feeding of gas and water. In addition, the device is provided with flat caps and hemispherical caps, making the design of experiments more flexible and practical.

The present invention enables dynamic monitoring of sand production and sand control during the experiments, analysis of changes of parameters in various stages during the simulation of sand production and sand control in the hydrate exploitation under predetermined conditions. The present invention also enables the prediction of sand production and gas production for different exploitation schemes and screen sizes, by analyzing the particle size of produced sands and the total volume of produced gas and liquid under different conditions of temperature, pressure, screen thickness, and material particle size.

BRIEF DESCRIPTION OF THE DRAWINGS

FIGS. 2A-2D show the structure of the reactor system, wherein FIG. 2A shows a left/right reactor unit, FIG. 2B shows a secondary reactor unit, FIG. 2C shows a central reactor unit, and FIG. 2D shows the accessories.

Figure 1:
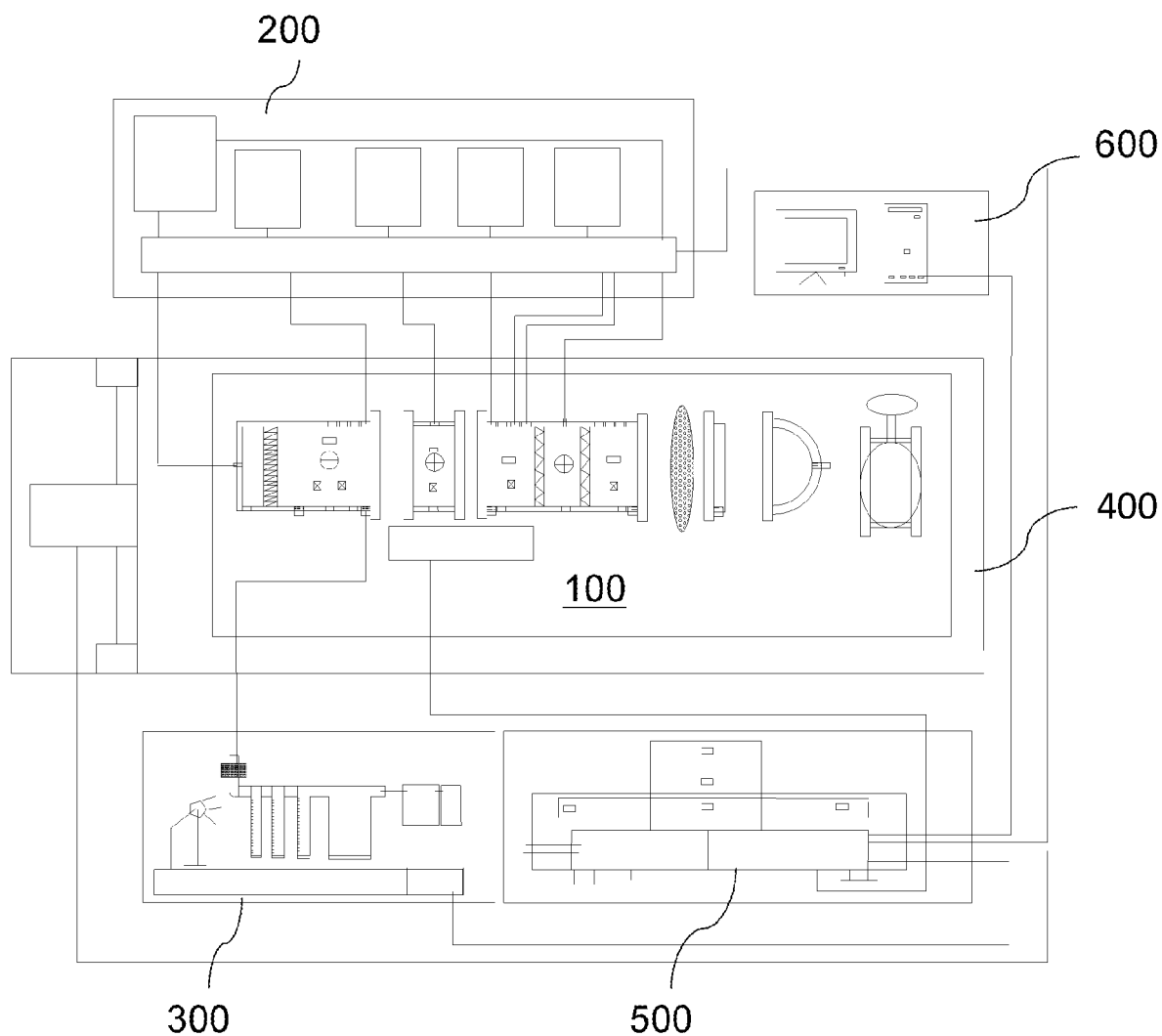
FIG. 1 shows the structure of the device.
Figure 2A:
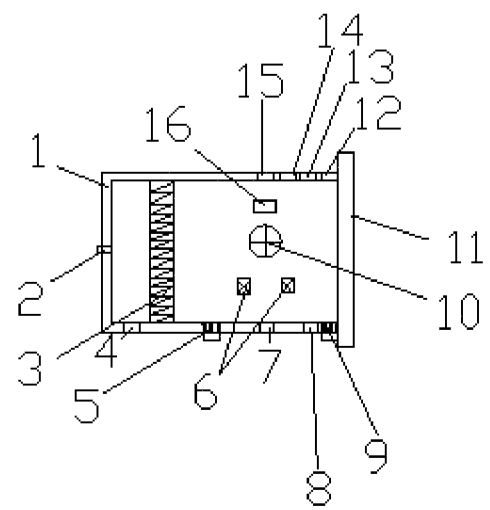
Figure 2B:
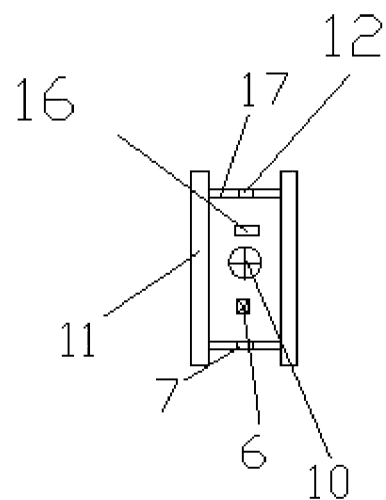
Figure 2C:
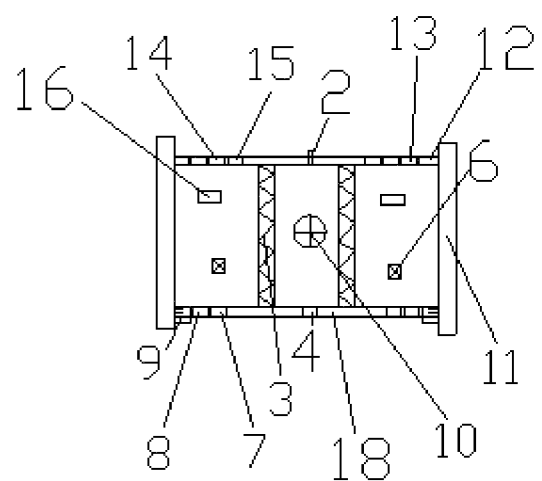
Figure 2D:
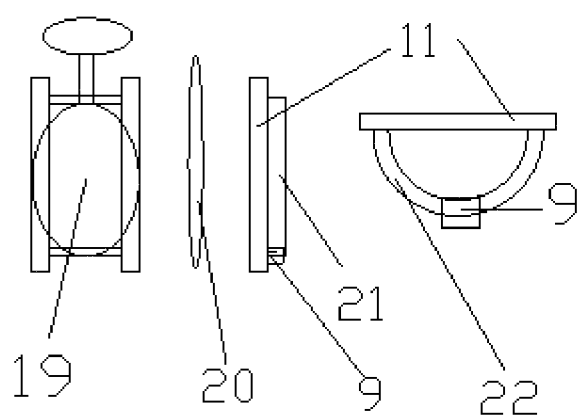
Figure 3:
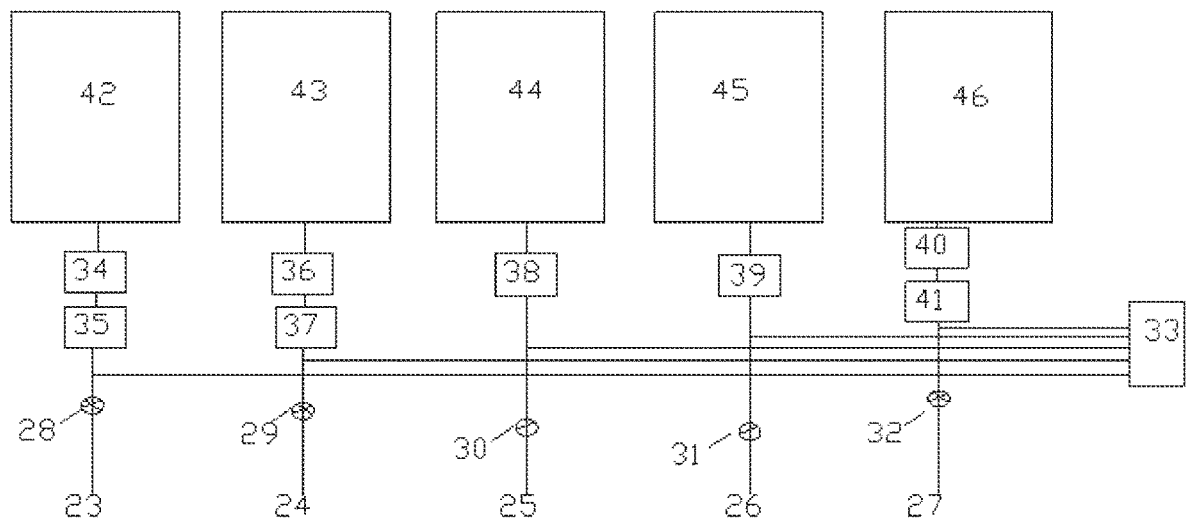
FIG. 3 shows the structure of the feeding system.
Figure 4:
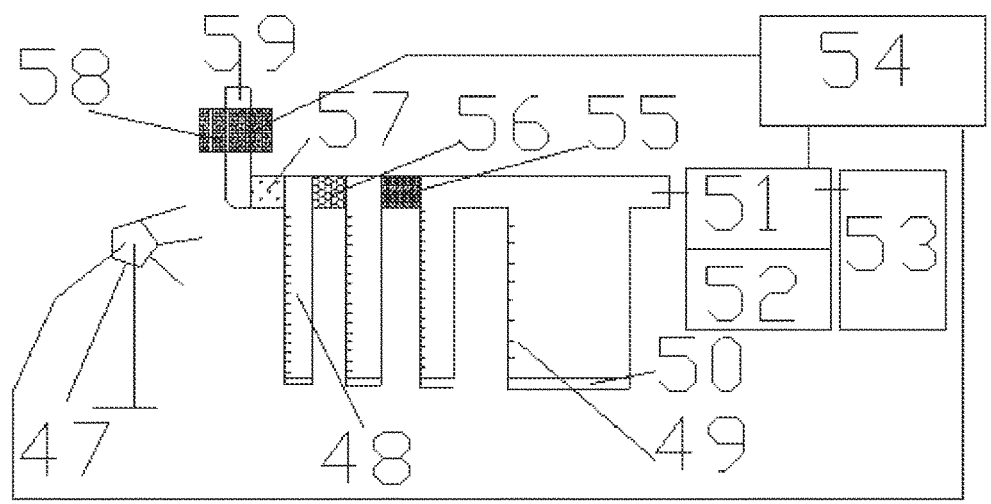
FIG. 4 shows the structure of the separation and measurement system.
Figure 5:
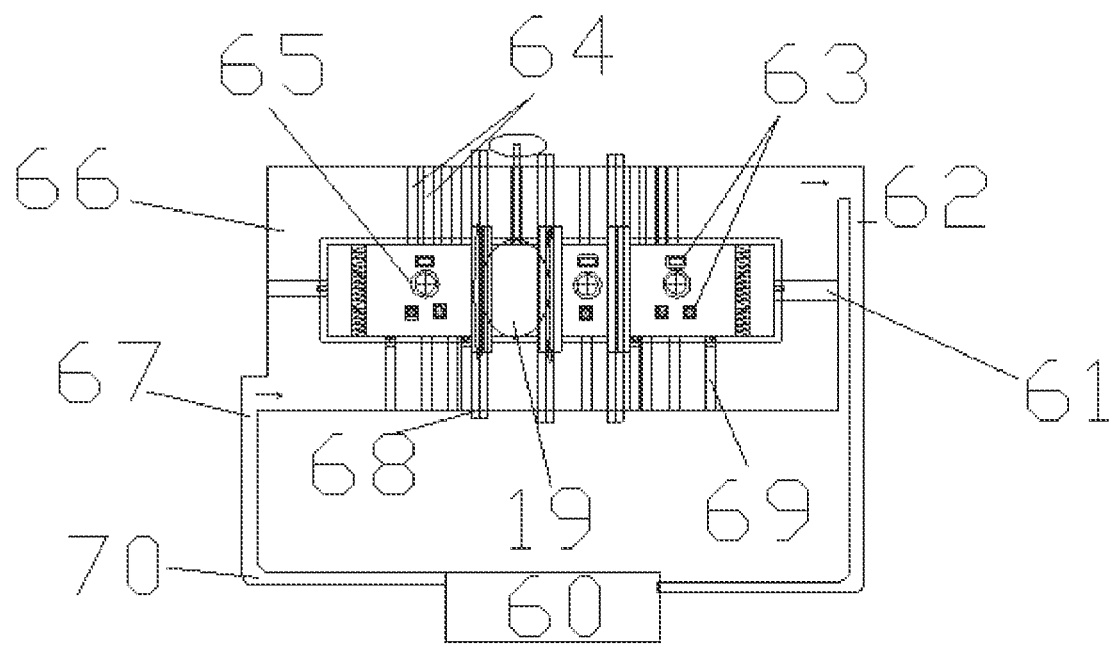
FIG. 5 shows the structure of the water-bath jacket system.
Figure 6:
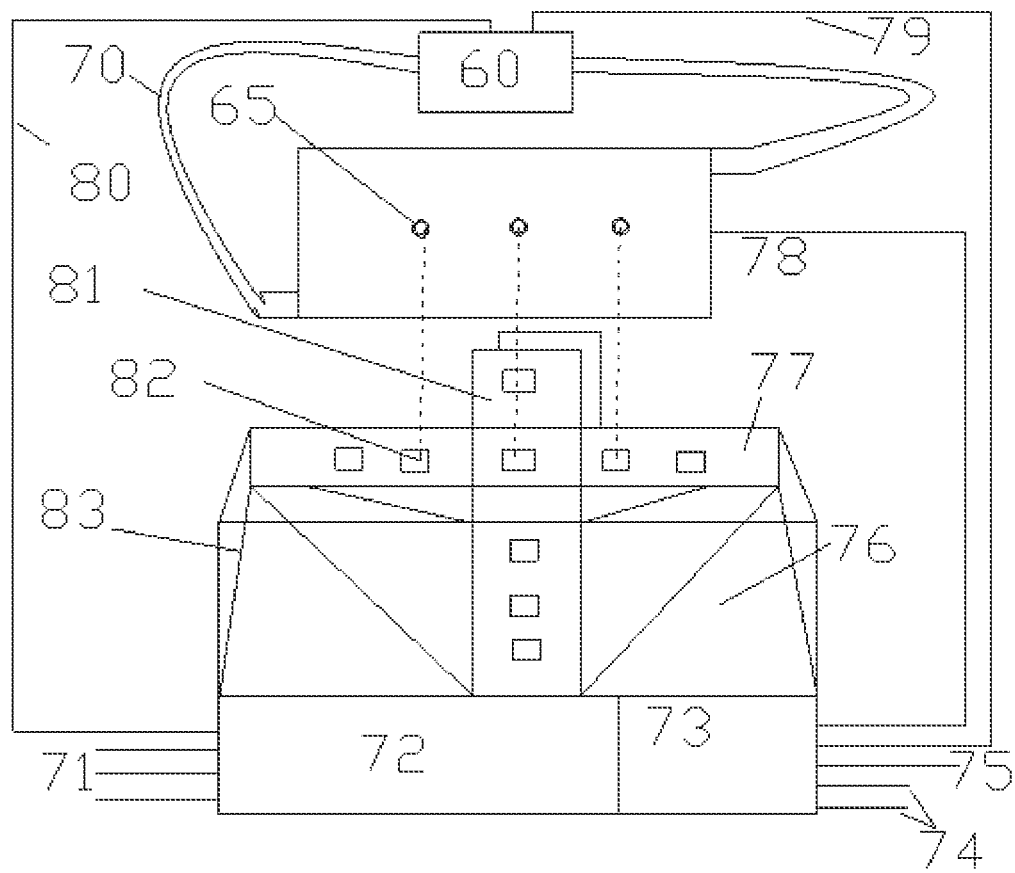
FIG. 6 shows the structure of the support and safety system.

Reference signs: 100, reactor system; 200, feeding system; 300, separation and measurement system; 400, water-bath jacket system; 500, support and safety system; 600, software recording and analyzing system;

1, wall of left/right reactor unit; 2, nitrogen inlet; 3, movable piston; 4, pressure relief opening; 5, auxiliary production outlet; 6, hole for sensor; 7, liquid discharging opening; 8, lower sight glass; 9, production outlet; 10, supporting nut; 11, flange; 12, sand inlet; 13, upper sight glass; 14, water inlet; 15, methane inlet; 16, hole for equipment; 17, wall of secondary reactor unit; 18, wall of central reactor unit; 19, ball valve; 20, mesh; 21, flat cap; 22, hemispherical cap; 23, connection point to nitrogen inlet; 24, connection point to water inlet; 25, connection point to sand inlet of sand control screen; 26, connection point to sand inlet of hydrate zone; 27, connection point to methane inlet; 28, nitrogen gas valve; 29, water valve; 30, screen sand barrier; 31, reservoir sand barrier; 32, methane gas valve; 33, data collector of the feeding system; 34, nitrogen gas flow meter; 35, nitrogen gas pressure gauge; 36, water flow meter; 37, water pressure gauge; 38, screen material-weighing device; 39, reservoir material-weighing device; 40, methane gas flow meter; 41, methane gas pressure gauge; 42, nitrogen gas supply; 43, water supply; 44, screen material supply; 45, reservoir material supply; 46, methane gas supply; 47, camera; 48, sand-measuring cylinder; 49, water-measuring cylinder; 50, cylinder sealing cover; 51, cylinder outlet flow meter; 52, cylinder outlet pressure gauge; 53, gas-collecting tank; 54, data collector of the separation and measurement system; 55, fine sand screen; 56, intermediate sand screen; 57, coarse sand screen; 58, reducing valve; 59, connection port to production outlet; 60, thermostat; 61, passage mating with nitrogen inlet; 62, temperature-controlling water outlet; 63, passage mating with hole for equipment or sensor; 64, passage mating with hole on upper wall of reactor; 65, fixing nut and passage for the fixing nut; 66, jacket casing; 67, temperature-controlling water inlet; 68, flange connection; 69, passage mating with hole on lower wall of reactor; 70, hose connection; 71, power output; 72, Safety interlocks such as distribution boxes/air circuit breakers/electric relays; 73, total input; 74, data input of each system and power input; 75, total output; 76, base; 77, horizontal fixing rod; 78, wiring of sensors and equipment of the reactor; 79, wiring of the temperature controlling device; 80, power supply of the temperature controlling device; 81, vertical fixing rod; 82, fixing hole; 83, base support.

DETAILED DESCRIPTION OF THE EMBODIMENTS

The content of the present invention will be further described in detail below with reference to the drawings and specific embodiments.

Embodiment

In the present embodiment, in order to better describe the combination of the system, the first reactor unit(s), the second reactor unit(s), and the third reactor unit(s) are respectively called the left/right reactor unit(s), the secondary left/right reactor unit(s), and the central reactor unit(s), while the reactor system may be called a reactor for short. Depending on the needs, the exploitation method can be selected from the depressurization method and the thermal stimulation method, wherein the depressurization method is one of the currently major methods for hydrate exploitation, which involves a dissociation process of hydrate solids to produce methane gas, caused by reducing the pressure on the gas hydrate layer to lower than the phase equilibrium pressure of hydrate under the local temperature. Design of exploitation wells for the depressurization method is similar to those for conventional exploitation of oil and gas; the pressure spreads quickly in the hydrate reservoir with higher permeability, and thus the depressurization method is the most potential method which is economical and effective. The thermal stimulation method refers to a process of heating the gas hydrate layer to raise its temperature to above the equilibrium temperature, which causes the gas hydrate to dissociate into water and natural gas.

The divisible device of the present invention, designed for sand production and sand control experiment for natural gas hydrate exploitation, comprises: a reactor system 100, a feeding system 200, a separation and measurement system 300, a water-bath jacket system 400, a support and safety system 500, and a software recording and analyzing system 600.

As shown are the wall 1 of left/right reactor unit, the wall 17 of secondary reactor unit, and the wall 18 of central reactor unit. The three reactor units are all cylinder-shaped pipes. Supporting nuts 10, holes 16 for equipment, and holes 6 for sensors are provided on both sides of the wall of each unit to support the reactor unit and allow regulating and collecting parameters. The three types of reactor units can be connected to each other via flanges 11. The three types of reactor units are each provided with pressure relief openings 4 and liquid discharging openings 7 at the bottom to enable reducing the pressure inside the reactor unit and discharging the liquid/solid from the reactor unit and the subsequent cleaning. The left/right reactor unit has a first end being open and a second end being closed, while the secondary reactor unit and the central reactor unit each has a symmetric structure with both ends being open. The movable piston 3 in each left/right reactor unit or central reactor unit is removable, and is used in combination with the nitrogen gas, which is introduced into the unit via the nitrogen inlet 2, to compress the filling materials in the reactor unit. On each of the wall 1 of left/right reactor unit and the wall 18 of central reactor unit, is provided with a sand inlet 12, a water inlet 14, and a methane inlet 15 to allow introducing sand, water, and gas into the unit. On each of the wall 1 of left/right reactor unit and the wall 18 of central reactor unit, at both the upper side and lower side, is provided with an upper sight glass 13 and a lower sight glass 8 configured to allow real-time inspection on the sand production and changes inside each unit of the reactor system during the exploitation process and experiment process. Further, on each of the wall 1 of left/right reactor unit and the wall 18 of central reactor unit, is provided with a production outlet 9 (the wall 1 may be further provided with a second production outlet). The ball valve 19 and the mesh 20 are provided between two reactor units (which are configured to serve as a hydrate zone and a sand control screen zone), in order to simulate the actual separation between the hydrate reservoir and the borehole wall or screen. Flat caps 21 and hemispherical caps 22 allow effective sealing of the reactor units in a simple sand-production/sand-control experiment; also, production outlets are provided at the bottom of each cap to allow sand production during the exploitation process. The hemispherical caps 22 can be used in the construction of vertical reactor systems, wherein the hemispherical shape allows complete collection of the produced sands.

In the feeding system, the nitrogen gas flow meter 34, the nitrogen gas pressure gauge 35, the water flow meter 36, the water pressure gauge 37, the screen material-weighing device 38, the reservoir material-weighing device 39, the methane gas flow meter 40, and the methane gas pressure gauge 41 allow the measurement to the flow rate, pressure, and mass of the introduced water, gas, and sands; they also allow the real-time data collection via the data collector 33. The nitrogen gas valve 28, the water valve 29, and the methane gas valve 32 are configured to start/stop the flow of gas and liquid. The screen sand barrier 30 and the reservoir sand barrier 31 allow the sealing of the reactor unit. The nitrogen gas supply 42 and the methane gas supply 46 each consist of a nitrogen or methane gas cylinder and a gas compressor, and are configured to introduce nitrogen gas and/or methane gas to the reactor unit at a given pressure. The water supply 43 consists of a water tank with water that meets the requirements of experiment; the water supply 43 is configured to supply water to the hydrate zone (for the formation of hydrate) and the view zone. The screen material supply 44 and the reservoir material supply 45, depending on the experiment requirements, may contain materials of different components and types, allowing study with different materials to realize the selection of proper screen materials, optimization based on the reservoir sand properties, and study on porous flow. The connection points 23, 24, 25, 26, and 27 in the figure are used to indicate how the supplies are respectively connected to the nitrogen inlet 2, the water inlet 14, the sand inlets 12 (of sand control screen and the hydrate zone), and the methane inlet 15, of the reactor system.

The separation and measurement system is connected to the production outlet 9 of the reactor system via the connection port 59 in order to allow the inflow of produced gas/water/sands during the simulated exploitation process. The reducing valve 58 is configured to reduce the pressure of the inflow to a proper range suitable for conducting separation. Sand-measuring cylinders 48 are provided to collect the sands, filtered by the coarse sand screen 57, the intermediate sand screen 56, and the fine sand screen 55, within the corresponding particle size range. A water-measuring cylinder 49 is provided to measure the amount of produced water during the sand-production process. The sand-measuring cylinders 48 and the water-measuring cylinder 49 are each provided with an unscrewable threaded cap at the bottom, for removing the sands and water after the experiment. A cylinder sealing cover 50 is further provided at the bottom of the water-measuring cylinder 49. The gas produced during the exploitation flows through a cylinder outlet flow meter 51 and a cylinder outlet pressure gauge 52 and thereby enters a gas-collecting tank 53; this process enables the measurement of the gas. The camera 47 can record the dynamic process during the gas-water-sand separation. Data from the camera 47, the reducing valve 58, the cylinder outlet flow meter 51, and the cylinder outlet pressure gauge 52 are collected by the data collector 54 of the separation and measurement system.

The water-bath jacket system consists of three parts: a thermostat 60, a hose connection 70, and a jacket casing 66. The thermostat 60 is configured to regulate a temperature of water inflowing from the temperature-controlling water outlet 62 through a hose, and send the water through another hose to the temperature-controlling water inlet 67. The jacket casing 66 encases the reactor units, wherein the passages 61 mating with nitrogen inlets, the passages 63 mating with holes for equipment or sensor, the passages 64 mating with holes on upper wall of the reactors, the passages 65 for the fixing nuts, and the passages 69 mating with holes on lower wall of reactors, are configured to allow the inlets/outlets/sensors of the reactor units to reach outside through the casing. The gap between the reactor units and the jacket casing 66 is filled with temperature-controlling water to produce the temperature conditions for simulated exploitation. The jacket casing 66 consists of multiple sections, wherein sealing between each two adjacent sections is realized by flange connection 68.

The support and safety system consists of a base 76, the data input and power input 74 of each system, and a total output 75, constituting three parts which include structure support, data measuring and collecting, and power management. Power input (among the data and power input 74) and power output 71 are configured to connect the safety interlocks 72 such as distribution boxes/air circuit breakers/electric relays with each system (such as connecting to the power supply 80 of the temperature controlling device) to realize power management. The data input of each system (among the data and power input 74) is connected to the total input 73 where they are connected together and thereby connected via a total output 75 to a computer; the recording and analysis of collected data and the controlling of each equipment are realized by software on the computer. The data input of each system includes wiring 78 of sensors and equipment of the reactor and wiring 79 of the temperature controlling device. The base 76 consists of horizontal fixing rods 77, vertical fixing rods 81, and a base support 83. Fixing holes are formed on the horizontal fixing rods 77 and the vertical fixing rods 81, configured to realize fixing in combination with the supporting nuts 10 and the fixing nut and passage 65 for the fixing nut, which allows the reactor and the jacket to be fixed on the base 76.

The function and simulation of each combination will be described below.

Figure 7A:
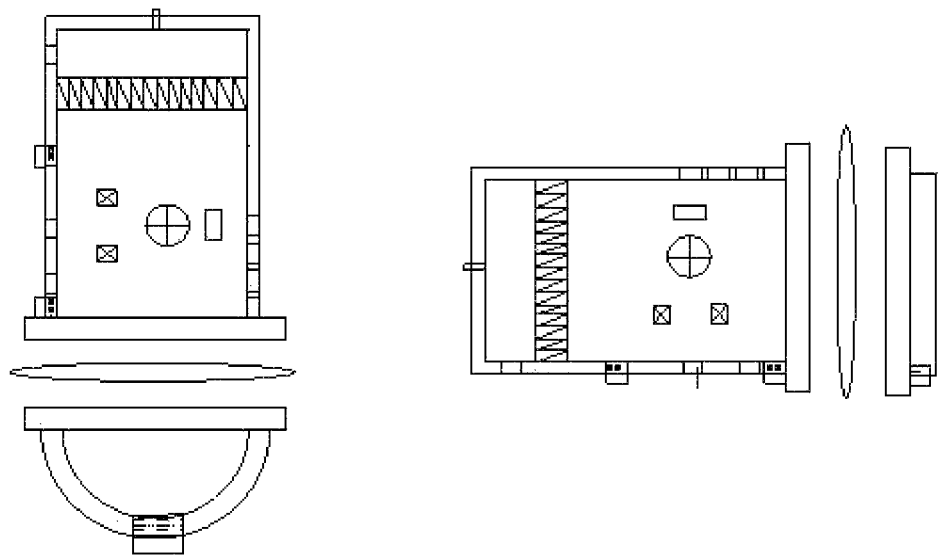
FIG. 7A shows simplest combinations of the reactor system.
Figure 7B:
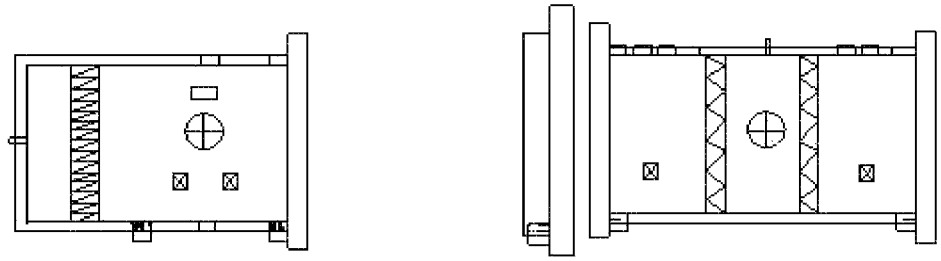
FIG. 7B shows substitution of units of the reactor system.

FIGS. 7A-7B show the simplest combination, which consists of a left reactor unit, a mesh 20, and a hemispherical cap 22 or flat cap 21. Generally, the flat cap 21 is used for a horizontal arrangement, while the hemispherical cap 22 is used for a vertical arrangement, which allows full collection of the produced sands. In this simplest combination, the left reactor unit constitutes a hydrate zone, where the hemispherical cap 22 or flat cap 21 is configured to collect the produced sands during the hydrate dissociation process and thereby discharge the sands.

In all combination as shown in FIG. 7A to FIG. 13C, the left reactor unit is equivalent to and can be interchanged with a combination of a central reactor unit and flat cap 21, since the wall 18 of the central reactor unit is provided with all the inlets, view zones, and production outlets that are provided on the wall 1 of the left unit. The arrows in FIG. 8A to FIG. 13C indicate the direction of flow of the produce sands during the hydrate dissociation process. Simulation of sand control screens is realized by providing a mesh 20 on each end of the secondary reactor unit.

Figure 8A:
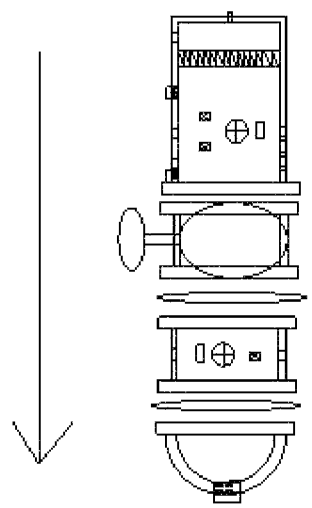
FIGS. 8A-8C show three combinations for simulation experiments with no view zone and one well.
Figure 8B:
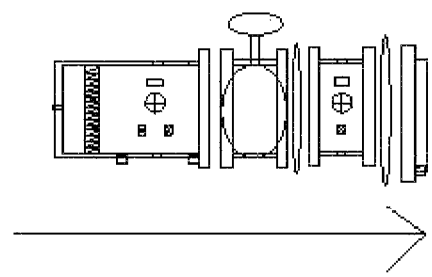
Figure 8C:
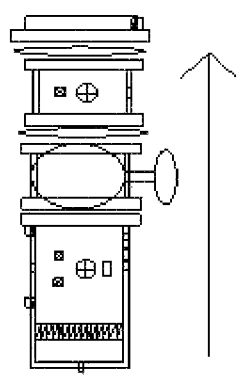

As shown in FIGS. 8A-8C, for simulation experiments with no view zone and one well, three combinations are shown from left to right. In the first combination (FIG. 8A), the reactor system is vertically assembled in an order (from top to bottom) of a hydrate zone, a sand control screen zone, and a sand production outlet, to carry out the simulation experiments with the sand control screens being disposed below the natural gas hydrate reservoir. In the second combination (FIG. 8B), the reactor system is horizontally assembled in an order (from left to right) of a hydrate zone, a sand control screen zone, and a sand production outlet, to carry out the simulation experiments with the sand control screens being disposed on the right side of the natural gas hydrate reservoir. In the third combination (FIG. 8C), the reactor system is vertically assembled in an order (from bottom to top) of a hydrate zone, a sand control screen zone, and a sand production outlet, to carry out the simulation experiments with the sand control screens being disposed above the natural gas hydrate reservoir.

Figure 9A:
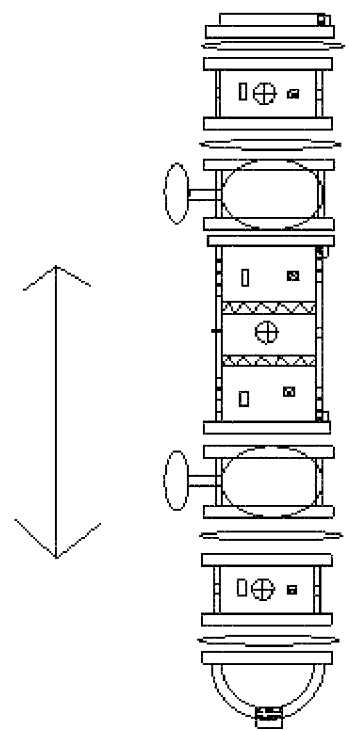
FIGS. 9A-9B show two combinations for simulation experiments with no view zone and two wells.
Figure 9B:
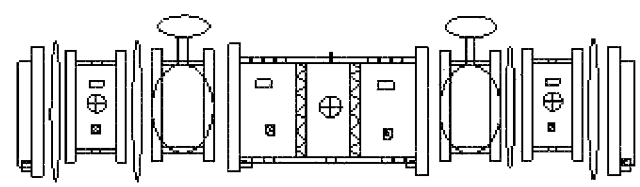
Figure 10A:
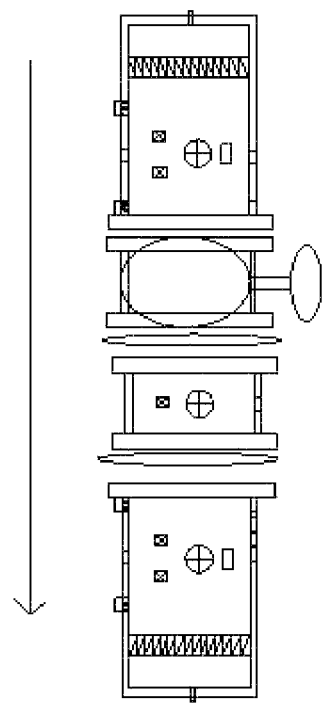
FIGS. 10A-10D show four combinations for simulation experiments with one view zone and one well.
Figure 10B:
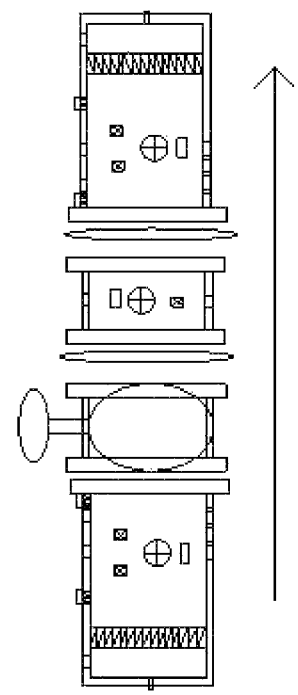
Figure 10C:
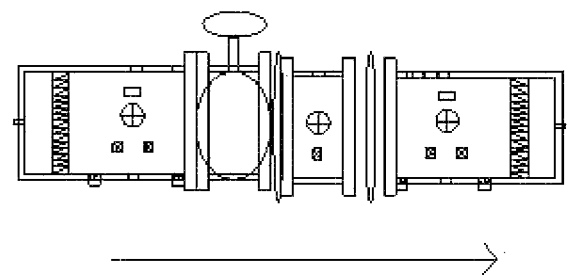
Figure 10D:
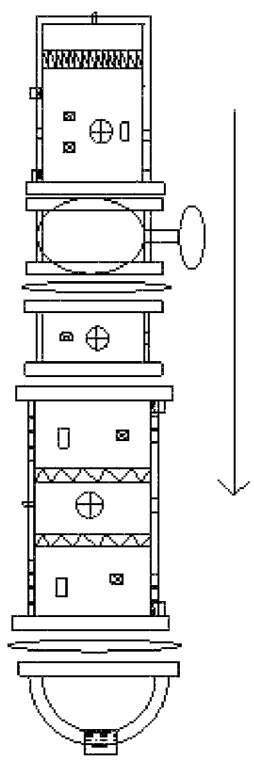

As shown in FIGS. 9A-9B, for simulation experiments with no view zone and two wells, two combinations are shown from left to right. In the first combination (FIG. 9A), the reactor system is vertically assembled in an order (from top to bottom) of a sand production outlet, a sand control screen zone, a hydrate zone, a sand control screen zone, and a sand production outlet, to carry out the simulation experiments with the sand control screens being disposed above and below the natural gas hydrate reservoir. In the second combination (FIG. 9B), the reactor system is horizontally assembled in an order (from left to right) of a sand production outlet, a sand control screen zone, a hydrate zone, a sand control screen zone, and a sand production outlet, to carry out the simulation experiments with the sand control screens being disposed on both left and right sides of the natural gas hydrate reservoir. Whether a piston is required in the hydrate zone depends on actual demand; when it is necessary to compact the reservoir material in the reactor, the piston is disposed inside for compacting the reservoir material; if the reservoir material is compacted before placed into the central reactor unit through the opening of two ends, the piston is not required.

As shown in FIGS. 10A-10D, for simulation experiments with one view zone and one well, four combinations are shown from left to right. In the first combination (FIG. 10A), the reactor system is vertically assembled in an order (from top to bottom) of a hydrate zone, a sand control screen zone, a view zone, and a sand production outlet, to carry out the simulation experiments with the sand control screens being disposed below the natural gas hydrate reservoir. In the second combination (FIG. 10B), the reactor system is vertically assembled in an order (from bottom to top) of a hydrate zone, a sand control screen zone, a view zone, and a sand production outlet, to carry out the simulation experiments with the sand control screens being disposed above the natural gas hydrate reservoir. In the third combination (FIG. 10C), the reactor system is horizontally assembled in an order (from left to right) of a hydrate zone, a sand control screen zone, a view zone, and a sand production outlet, to carry out the simulation experiments with the sand control screens being disposed on the right side of the natural gas hydrate reservoir. In the fourth combination (FIG. 10D), the reactor system is vertically assembled in an order (from top to bottom) of a hydrate zone, a sand control screen zone, a view zone, and a sand production outlet, to carry out the simulation experiments with the sand control screens being disposed below the natural gas hydrate reservoir.

Figure 11A:
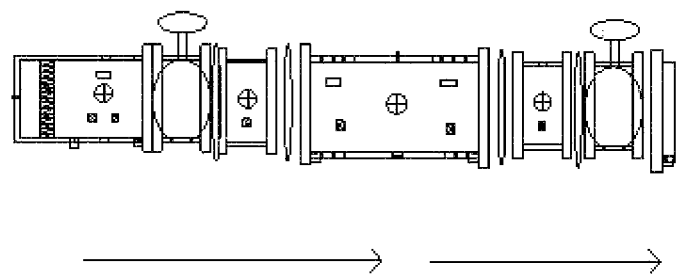
FIGS. 11A-11C show three combinations for simulation experiments with one view zone and two wells.
Figure 11B:
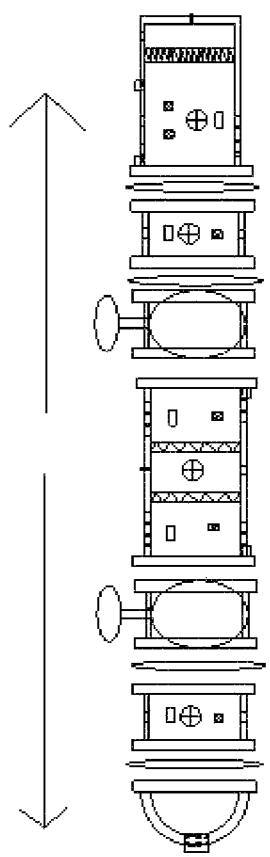
Figure 11C:
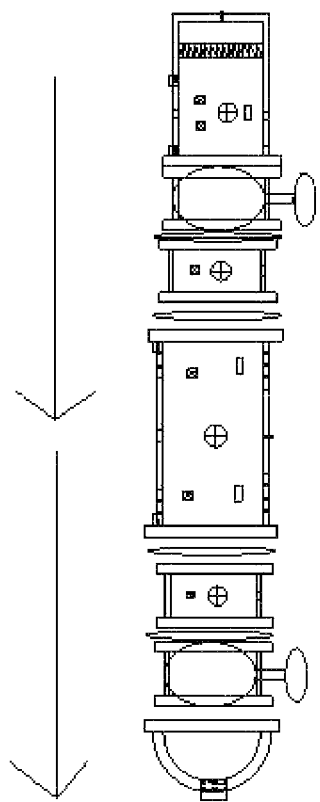

As shown in FIGS. 11A-11C, for simulation experiments with one view zone and two wells, three combinations are shown from left to right. In the first combination (FIG. 11A), the reactor system is horizontally assembled in an order (from left to right) of a hydrate zone, a sand control screen zone, a view zone, a sand control screen zone, and a sand production outlet, to carry out the simulation experiments with the sand control screens being disposed on the right side of the natural gas hydrate reservoir. In the second combination (FIG. 11B), the reactor system is vertically assembled in an order (from top to bottom) of a sand production outlet, a view zone, a sand control screen zone, a hydrate zone, a sand control screen zone, and a sand production outlet, to carry out the simulation experiments with the sand control screens being disposed both above and below the natural gas hydrate reservoir. In the third combination (FIG. 11C), the reactor system is vertically assembled in an order (from top to bottom) of a hydrate zone, a sand control screen zone, a view zone, a sand control screen zone, and a sand production outlet, to carry out the simulation experiments with the sand control screens being disposed below the natural gas hydrate reservoir. The two sand control screen zones and the two sand production outlets are for simulation of sand production via two screen sections.

Figure 12A:
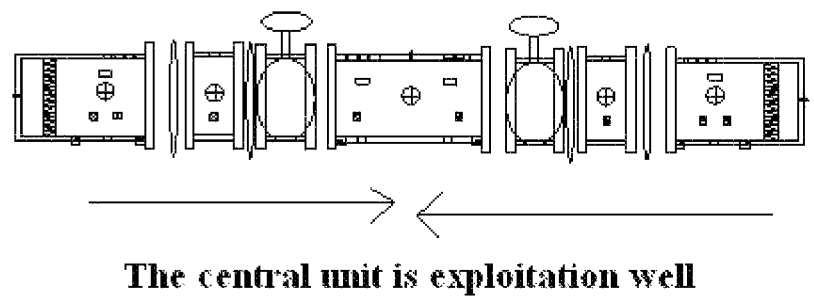
FIGS. 12A-12B show two combinations for simulation experiments with two view zones and one well.
Figure 12B:
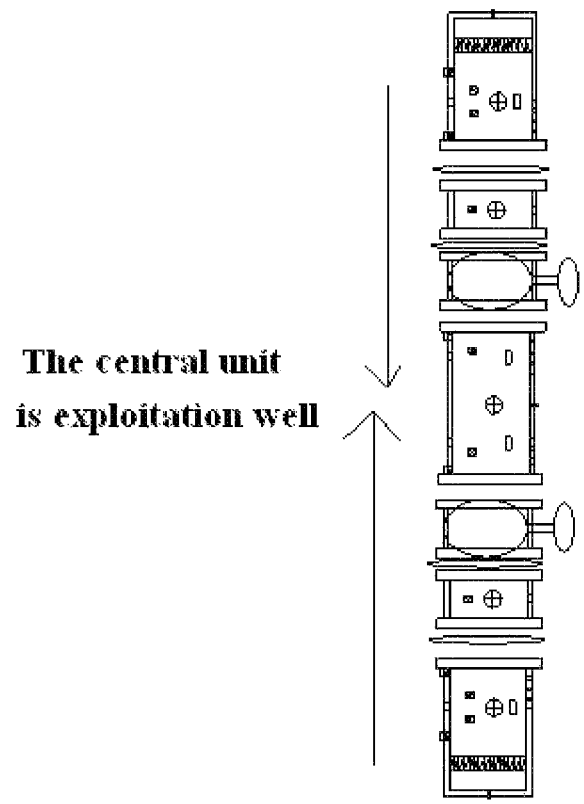

As shown in FIGS. 12A-12B, for simulation experiments with two view zones and one well, two combinations are shown from left to right. In the first combination (FIG. 12A), the reactor system is horizontally assembled in an order (from left to right) of a hydrate zone, a sand control screen zone, a sand production outlet, a view zone, a sand production outlet, a sand control screen zone, and a hydrate zone, to carry out the simulation experiments with two natural gas hydrate reservoirs being disposed on both sides of the sand control screens. In the second combination (FIG. 12B), the reactor system is horizontally assembled in an order (from top to bottom) of a hydrate zone, a sand control screen zone, a sand production outlet, a view zone, a sand production outlet, a sand control screen zone, and a hydrate zone, to carry out the simulation experiments with two natural gas hydrate reservoirs being disposed both above and below the sand control screens. The two combinations provide excellent simulation of sand production in vertical wells and horizontal wells during actual exploitation of hydrates.

Figure 13A:
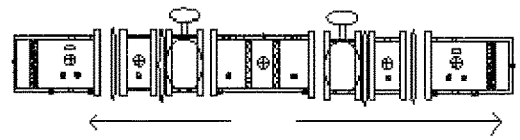
FIGS. 13A-13C show seven combinations for simulation experiments with two view zones and two wells.
Figure 13A:
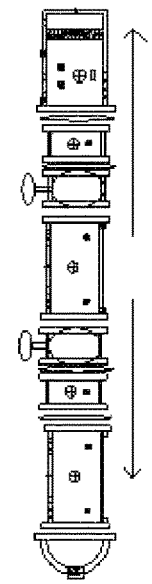
Figure 13B:
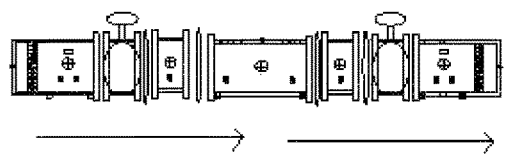
Figure 13B:
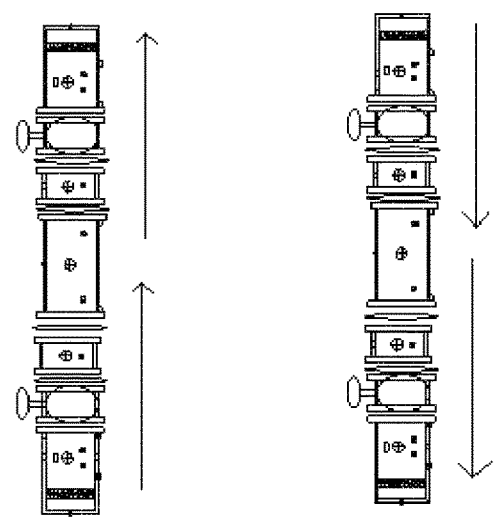
Figure 13C:
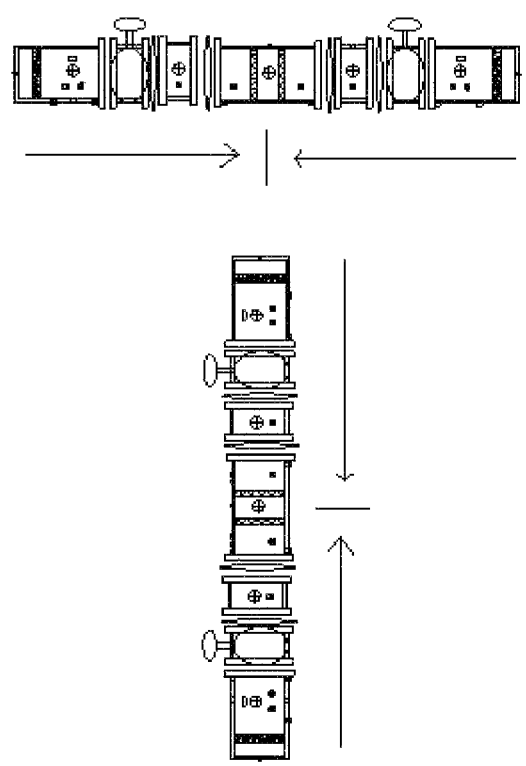

As shown in FIGS. 13A-13C, for simulation experiments with two view zones and two wells, seven combinations are shown from left to right and from the first row to the second row. In the first and second combinations (FIG. 13A), the reactor system is respectively horizontally and vertically assembled in an order (from center to each end) of a hydrate zone, a sand control screen zone, a view zone, and a sand production outlet to carry out the simulation experiments with the sand control screens being disposed above and below (or on both sides of) the natural gas hydrate reservoir, with directions of sand production in the two wells being opposite to each other; whether pistons are required depends on whether the reservoir material is compacted. In the third, fourth, and fifth combinations (FIG. 13B), the reactor system is respectively horizontally, vertically, and vertically assembled in an order (respectively from left, bottom, and top to the corresponding other end) of a hydrate zone, a sand control screen zone, a view zone, a sand production outlet, a sand control screen zone, a view zone, a sand production outlet, to carry out the simulation experiments with the sand control screens being disposed one the right side of, above, or below the natural gas hydrate reservoir, with directions of sand production in the two wells being identical to each other. In the sixth and seven combinations (FIG. 13C), the reactor system is respectively horizontally and vertically assembled in an order (from each end to center) of a hydrate zone, a sand control screen zone, a view zone, and a sand production outlet, to carry out the simulation experiments with two natural gas hydrate reservoirs being disposed on both sides of (or both above and below) the sand control screens, with directions of sand production in the two wells being opposite to each other.

The present invention is characterized in that the experimental device is modularized and thereby comprises a reactor system, a feeding system, a separation and measurement system, a water-bath jacket system, a support and safety system, and a software recording and analyzing system. In the reactor system, the reactor units can be combined in different ways depending on the experimental conditions and purposes. The reactor units mainly comprise: left/right reactor units, secondary reactor units, central reactor units, and caps. The combination of a left/right reactor unit with a cap gives a hydrate formation reactor without sand control screens. Combining the left/right reactor unit, secondary left/right reactor units and central reactor units with other accessories (such as valves, caps, and meshes) allows the reactor system to carry out the simulation experiments with either zero, one, or two view zones, and with either one or two wells. A left/right reactor unit or a central reactor unit can serve as a hydrate zone or view zone, and a secondary left/right reactor unit with a mesh provided at each end can serve as a sand control screen zone. The horizontal and vertical arrangement of the support can realize vertical and horizontal sand production/sand control experiment respectively.

A method for simulation experiments of sand production and sand control in natural gas hydrate exploitation, using different combinations of the present invention, will be further described below with FIGS. 2A-2D, FIG. 3, FIG. 4, FIG. 5, and FIG. 6.

The first step is to assemble the reactor system to give a combination according to a purpose of the simulation experiment. Described herein is an experiment for simulation of sand production/sand control with one view zone and two well as an example. According to the purpose, the reaction system is assembled in the way shown in FIGS. 11A-11C. The inner chamber of the left reactor serves as sand production view zone, wherein the nitrogen inlet 2 on its left end will be closed after the air in the chamber is eliminated, and the movable piston 3 in the left reactor unit will be placed against the left wall. The secondary reactor unit will be filled with screen material and then a mesh 20 will be provided on each end thereof. The central reactor unit is connected to a ball valve 19 at each end, and filled with reservoir material at both sides while nitrogen gas is introduced to the central area to compress the reservoir material at both sides. A flat cap at the most right side is provided to realize the complete sealing of the inner of the reactor system. Temperature and pressure sensors are respectively inserted into the corresponding holes 6; a resistance sensor may be inserted into a hole of the left reactor unit to measure the resistance in the view zone. The feeding system and the separation and measurement system are each connected to the reactor system via the corresponding inlets/outlets. After the system is assembled, the whole reactor system is placed in the water-bath jacket system, which is then fixed on a horizontal support of the support and safety system through the aid of fixing nuts 65 and supporting nuts 10.

The second step is to perform an air tightness test. After the reactor system and water-bath system are assembled, nitrogen gas is introduced to assess air tightness and eliminate other gases. Specifically, nitrogen gas is introduced to the left reactor unit and the central reactor unit through their nitrogen inlets (while all other inlets/outlets of the reactor units are closed) to a specific pressure, and air tightness will be confirmed when the pressure can maintain for a specific period.

The third step is to introduce material/gas and control temperature/pressure. The reactor units will be filed with a corresponding material via the feeding system, followed by the introduction of water and methane gas until it reaches a high pressure required by the experiment. Under such high pressure and a low temperature regulated by the water-bath jacket system, hydrates are gradually formed. Pressure change is monitored by the pressure sensors; when the system exhibits no change or just a small change in the pressure over a specific period, the formation of natural gas hydrates is deemed to be complete.

The next step is to measure and collect data of the exploitation process. At this moment, the simulation of exploitation and sand production is initiated. The separation and measurement system is connected to the reactor system via the connection port 59. The production outlet 9 of the view zone and the production outlet of the flat cap are opened to allow exploitation via the depressurization method, wherein the amounts of produced sands and water during the exploitation process will be measured. The reducing valve 58 will be regulated during the exploitation process, such that the produced sands of different particle sizes will be filtered by the coarse sand screen 57, the intermediate sand screen 56, and the fine sand screen 55, and thereby collected by the corresponding and-measuring cylinders 48. The gas produced during the exploitation flows through a cylinder outlet flow meter 51 and a cylinder outlet pressure gauge 52 and thereby enters a gas-collecting tank 53, which allows measurement on the produced gas. The camera 47 can record the dynamic process during the gas-water-sand separation. Data from the camera 47, the reducing valve 58, the cylinder outlet flow meter 51, and the cylinder outlet pressure gauge 52 are collected by the data collector 54 of the separation and measurement system.

The next step is to dissemble the system and analyze the data. When a pressure of produced gas reduces to a relatively lower value and stops changing, the simulated exploitation is deemed to be complete. Data collected by the sensors will be transmitted via the data input 74 of each system to the total input 73, in which the data may be subjected to signal processing, and then transmitted via the total output 75 to a computer in which the data will be recorded and analyzed in real time by software. After the experiment is finished, the power supply to the equipment is cut off, and then the gas in the reactor system will be released to reduce the pressure therein and collected by gas tank. Eventually, the reactor system will be cleaned and the material therein will be removed.

The above-mentioned embodiments are only intended to illustrate the technical concept and characteristics of the present invention, enabling those of ordinary skill in the art to understand the content of the present invention and implement them accordingly, but are not intended to limit the scope of the present invention. All equivalent changes or modifications made according to the essence of the present invention should fall within the scope of the present invention.

What is claimed is:

1. A divisible device for a simulation experiment of sand production and sand control in natural gas hydrate exploitation, comprising a reactor system, a feeding system, a separation and measurement system, a water-bath jacket system, a support and safety system, and a software recording and analyzing system; wherein
    the feeding system is configured to introduce gas, liquid, and sands into the reactor system to allow formation of natural gas hydrates in the reactor system;
    the reactor system is disposed in the water-bath jacket system, and the water-bath jacket system is configured to regulate a temperature inside the reactor system for simulating an ambient temperature of a natural gas hydrate reservoir;
    the support and safety system comprises a base, wherein the water-bath jacket system is vertically or horizontally fixable on the base for simulating the sand production and sand control by sand control screens at various positions in the natural gas hydrate reservoir;
    the base is provided with a data collecting module, wherein the data collecting module collects data from the reactor system during a simulated exploitation by a plurality of sensors;
    the separation and measurement system is connected to a production outlet of the reactor system for simulating a inflow of a gas-liquid-sand mixture during the simulated exploitation; the separation and measurement system is configured to separate and measure the gas-liquid-sand mixture, and send measurement data to the data collecting module;
    the software recording and analyzing system is communicatingly connected with the data collecting module;
    the reactor system comprises first reactor units, second reactor units, third reactor units, ball valves, meshes, and caps; each of the first reactor units comprises a cylindrical casing with a first end being open and a second end being closed; each of the second reactor units and the third reactor units comprises a cylindrical casing with both ends being open; the cylindrical casing of each of the first reactor units, the second reactor units, and the third reactor units is provided with holes for disposing sensors; the first reactor units, the second reactor units, and the third reactor units are each provided with a pressure relief opening and a liquid discharging opening; the first reactor units and the third reactor units are each further provided with a sand inlet, a water inlet, a methane inlet, a production outlet, and a sight opening; the caps are each provided with a production outlet; and
    the first reactor units, the second reactor units, the third reactor units, the ball valves, the meshes, and the caps are configured to be combined in a plurality of ways to allow the reactor system to carry out the simulation experiment with either zero, one, or two view zones, with either one or two wells, and with the sand control screens being disposed at various positions in the natural gas hydrate reservoir.

2. The divisible device of claim 1, wherein, the first reactor units and the third reactor units are further provided with moveable pistons, the second end of each of the first reactor units and the cylindrical casing of each of the third reactor units is provided with a nitrogen inlet configured to introduce nitrogen gas to drive the moveable pistons move toward the ends where materials are fed, wherein,
    each of the first reactor units is provided with one movable piston, wherein the one movable piston is movable toward the first end of the first reactor unit during operation, and
    each of the third reactor units is provided with two movable pistons, wherein the two movable pistons are each moveable toward either end of the third reactor unit during operation.

3. The divisible device of claim 2, wherein, the reactor system is configured to carry out the simulation experiment with no view zone and one well, by assembling in an order of first reactor unit, ball valve, mesh, second reactor unit, mesh, and cap, wherein the first reactor unit is configured to simulate a hydrate zone, the combination of ball valve, mesh, second reactor unit, and mesh is configured to simulate a sand control screen zone, and the cap is configured to simulate a sand production outlet;
    wherein the reactor system being vertically assembled with the cap being disposed at bottom allows to carry out the simulation experiment with the sand control screens being disposed below the natural gas hydrate reservoir; or
    the reactor system being horizontally assembled allows to carry out the simulation experiment with the sand control screens being disposed laterally to the natural gas hydrate reservoir; or
    the reactor system being vertically assembled with the cap being disposed at top allows to carry out the simulation experiment with the sand control screens being disposed above the natural gas hydrate reservoir.

4. The divisible device of claim 3, wherein, the caps are hemispherical caps when the reactor system is vertically assembled, or the caps are flat caps when the reactor system is horizontally assembled; a combination of one third reactor unit and one cap is equivalent to one first reactor unit.

5. The divisible device of claim 2, wherein, the reactor system is configured to carry out the simulation experiment with no view zone and two wells, by assembling in an order of cap, mesh, second reactor unit, mesh, ball valve, third reactor unit, ball valve, mesh, second reactor unit, mesh, and cap, wherein the third reactor unit is configured to simulate a hydrate zone, each combination of ball valve, mesh, second reactor unit, and mesh is configured to simulate a sand control screen zone, and each cap is configured to simulate a sand production outlet;
   wherein the reactor system being vertically assembled allows to carry out the simulation experiment with the sand control screens being disposed above and below the natural gas hydrate reservoir; or
   the reactor system being horizontally assembled allows to carry out the simulation experiment with the sand control screens being disposed laterally to the natural gas hydrate reservoir.

6. The divisible device of claim 5, wherein, the caps are hemispherical caps when the reactor system is vertically assembled, or the caps are flat caps when the reactor system is horizontally assembled; a combination of one third reactor unit and one cap is equivalent to one first reactor unit.

7. The divisible device of claim 2, wherein, the reactor system is configured to carry out the simulation experiment with one view zone and one well, by assembling in an order of first reactor unit, ball valve, mesh, second reactor unit, mesh, and first reactor unit, wherein the first reactor unit adjacent to the ball valve is configured to simulate a hydrate zone, the combination of ball valve, mesh, second reactor unit, and mesh is configured to simulate a sand control screen zone, and the first reactor unit far away from the ball valve is configured to simulate the view zone and a sand production outlet;
   wherein the reactor system being vertically assembled with the ball valve being disposed at an upper side allows to carry out the simulation experiment with the sand control screens being disposed below the natural gas hydrate reservoir, wherein, the first reactor unit far away from the ball valve is equivalent to a combination of one third reactor unit and one cap; or
   the reactor system being vertically assembled with the ball valve being disposed at a lower side allows to carry out the simulation experiment with the sand control screens being disposed above the natural gas hydrate reservoir; or
   the reactor system being horizontally assembled allows to carry out the simulation experiment with the sand control screens being disposed laterally to the natural gas hydrate reservoir.

8. The divisible device of claim 7, wherein, the caps are hemispherical caps when the reactor system is vertically assembled, or the caps are flat caps when the reactor system is horizontally assembled; a combination of one third reactor unit and one cap is equivalent to one first reactor unit.

9. The divisible device of claim 2, wherein, the reactor system is configured to carry out the simulation experiment with one view zone and two wells, by assembling in an order of first reactor unit, ball valve, mesh, second reactor unit, mesh, third reactor unit, mesh, second reactor unit, mesh, ball valve, and cap, wherein:
   the reactor system being horizontally assembled in an order of first reactor unit, ball valve, mesh, second reactor unit, mesh, third reactor unit, mesh, second reactor unit, mesh, ball valve, and cap allows to carry out the simulation experiment with the sand control screens being disposed laterally to the natural gas hydrate reservoir, wherein, the first reactor unit is configured to simulate a hydrate zone, the combination of ball valve, mesh, second reactor unit, and mesh is configured to simulate a sand control screen zone; the third reactor unit is configured to simulate the view zone and a sand production outlet, the combination of mesh, second reactor unit, mesh, and ball valve is configured to simulate another sand control screen zone, and the cap is configured to simulate another sand production outlet; or
   the reactor system being vertically assembled in an order of first reactor unit, ball valve, mesh, second reactor unit, mesh, third reactor unit, mesh, second reactor unit, mesh, ball valve, and cap allows to carry out the simulation experiment with the sand control screens being disposed below the natural gas hydrate reservoir, wherein, the first reactor unit is configured to simulate a hydrate zone, the combination of ball valve, mesh, second reactor unit, and mesh is configured to simulate a sand control screen zone, the third reactor unit is configured to simulate the view zone and a sand production outlet, the combination of mesh, second reactor unit, mesh, and ball valve is configured to simulate another sand control screen zone, and the cap is configured to simulate another sand production outlet; or
   the reactor system being vertically assembled in an order of first reactor unit, mesh, second reactor unit, mesh, ball valve, third reactor unit, ball valve, mesh, second reactor unit, mesh, and cap allows to carry out the simulation experiment with the sand control screens being disposed above and below the natural gas hydrate reservoir, wherein, the first reactor unit is configured to simulate the view zone and a sand production outlet, the combination of mesh, second reactor unit, mesh, and ball valve is configured to simulate a sand control screen zone, and the third reactor unit is configured to simulate a hydrate zone.

10. The divisible device of claim 9, wherein, the caps are hemispherical caps when the reactor system is vertically assembled, or the caps are flat caps when the reactor system is horizontally assembled; a combination of one third reactor unit and one cap is equivalent to one first reactor unit.

11. The divisible device of claim 2, wherein, the reactor system is configured to carry out the simulation experiment with two view zones and one well, by assembling in an order of first reactor unit, mesh, second reactor unit, mesh, ball valve, third reactor unit, ball valve, mesh, second reactor unit, mesh, and cap, wherein, the first reactor unit is configured to simulate a hydrate zone, each combination of mesh, second reactor unit, mesh, and ball valve is configured to simulate a sand control screen zone, and the third reactor unit is configured to simulate the view zones and a sand production outlet;
   wherein the reactor system being horizontally assembled allows to carry out the simulation experiment with two natural gas hydrate reservoirs being disposed on both sides of the sand control screens; or
   the reactor system being vertically assembled allows to carry out the simulation experiment with two natural gas hydrate reservoirs being disposed both above and below the sand control screens.

12. The divisible device of claim 11, wherein, the caps are hemispherical caps when the reactor system is vertically assembled, or the caps are flat caps when the reactor system is horizontally assembled; a combination of one third reactor unit and one cap is equivalent to one first reactor unit.

13. The divisible device of claim 2, wherein, the reactor system is configured to carry out the simulation experiment with two view zones and two wells, by assembling in an order of first reactor unit, mesh, second reactor unit, mesh, ball valve, third reactor unit, ball valve, mesh, second reactor unit, mesh, and cap, wherein:

the reactor system being horizontally or vertically assembled in an order of first reactor unit, mesh, second reactor unit, mesh, ball valve, third reactor unit, ball valve, mesh, second reactor unit, mesh, and cap allows to carry out the simulation experiment with the sand control screens being disposed at both sides of the natural gas hydrate reservoir, wherein, the third reactor unit is configured to simulate a hydrate zone, each combination of mesh, second reactor unit, mesh, and ball valve is configured to simulate a sand control screen zone, the first reactor unit is configured to simulate one view zone, and the cap is configured to simulate a sand production outlet; or the reactor system being horizontally assembled in an order of first reactor unit, ball valve, mesh, second reactor unit, mesh, third reactor unit, mesh, second reactor unit, mesh, ball valve, and cap allows to carry out the simulation experiment with the sand control screens being disposed laterally to the natural gas hydrate reservoir and with directions of sand production in the two wells being identical to each other, wherein, the first reactor unit is configured to simulate a hydrate zone, each combination of ball valve, mesh, second reactor unit, mesh is configured to simulate a sand control screen zone, the third reactor unit is configured to simulate one view zone and a sand production outlet, and the first reactor unit is configured to simulate another view zone and another sand production outlet; or the reactor system being vertically assembled in an order of first reactor unit, ball valve, mesh, second reactor unit, mesh, third reactor unit, mesh, second reactor unit, mesh, ball valve, and cap from bottom to up allows to carry out the simulation experiment with the sand control screens being disposed above the natural gas hydrate reservoir and with directions of sand production in the two wells being identical to each other, wherein, the first reactor unit is configured to simulate a hydrate zone, each combination of ball valve, mesh, second reactor unit, mesh is configured to simulate a sand control screen zone, the third reactor unit is configured to simulate one view zone and a sand production outlet, and the first reactor unit is configured to simulate another view zone and another sand production outlet; or the reactor system being vertically assembled in an order of first reactor unit, ball valve, mesh, second reactor unit, mesh, third reactor unit, mesh, second reactor unit, mesh, ball valve, and cap from up to bottom allows to carry out the simulation experiment with the sand control screens being disposed below the natural gas hydrate reservoir and directions of sand production in the two wells being identical to each other, wherein, the first reactor unit is configured to simulate a hydrate zone, each combination of ball valve, mesh, second reactor unit, mesh is configured to simulate a sand control screen zone, the third reactor unit is configured to simulate one view zone and a sand production outlet, and the first reactor unit is configured to simulate another view zone and another sand production outlet; or the reactor system being horizontally or vertically assembled in an order of first reactor unit, ball valve, mesh, second reactor unit, mesh, third reactor unit, mesh, second reactor unit, mesh, ball valve, and cap allows to carry out the simulation experiment with two natural gas hydrate reservoirs being disposed on both sides of the sand control screens and directions of sand production in the two wells being opposite to each other, wherein, the first reactor unit is configured to simulate a hydrate zone, each combination of ball valve, mesh, second reactor unit, mesh is configured to simulate a sand control screen zone, and the third reactor unit is configured to simulate one view zone and a sand production outlet.

14. The divisible device of claim 13, wherein, the caps are hemispherical caps when the reactor system is vertically assembled, or the caps are flat caps when the reactor system is horizontally assembled; a combination of one third reactor unit and one cap is equivalent to one first reactor unit.

15. The divisible device of claim 2, wherein, the caps are hemispherical caps when the reactor system is vertically assembled, or the caps are flat caps when the reactor system is horizontally assembled; a combination of one third reactor unit and one cap is equivalent to one first reactor unit.

16. The divisible device of claim 1, wherein, the caps are hemispherical caps when the reactor system is vertically assembled, or the caps are flat caps when the reactor system is horizontally assembled; a combination of one third reactor unit and one cap is equivalent to one first reactor unit.

17. A method for a simulation experiment of sand production and sand control in natural gas hydrate exploitation using the divisible device of claim 1, comprising the following steps:

assembling the reactor system to give a combination according to a purpose of the simulation experiment, placing a reservoir material partially in a corresponding reactor unit according to the combination, disposing sensors in the corresponding holes, wherein the sensors include pressure sensors, temperature sensors, and resistance sensors;

connecting the feeding system and the separation and measurement system to the corresponding inlets or outlets of the reactor system, vertically or horizontally disposing the reactor system in the water-bath jacket system, and fixing the in the water-bath jacket system on the base;

performing an air tightness test on the reactor system and the water-bath jacket system;

filling the corresponding reactor unit with the reservoir material, introducing water and methane gas into the reactor system to a predetermined pressure according to the simulation experiment to initiate the formation of the natural gas hydrates under the predetermined pressure and the temperature regulated by the water-bath jacket system; monitoring a pressure change in the reactor system via the pressure sensors, wherein the formation of the natural gas hydrates is complete when the pressure change in a specific period is zero or below a predetermined value;

performing the simulated exploitation via a depressurization method, and separating and measuring the gas-liquid-sand mixture via the separation and measurement system;

when a pressure of produced gas reduces to a predetermined value and stops changing, terminating the simulated exploitation, and sending the measurement data to the software recording and analyzing system via the support and safety system.

18. The method of claim 17, wherein, the first reactor units and the third reactor units are further provided with moveable pistons, the second end of each of the first reactor units and the cylindrical casing of each of the third reactor units is provided with a nitrogen inlet configured to introduce nitrogen gas to drive the moveable pistons move toward the ends where materials are fed, wherein, each of the first reactor units is provided with one movable piston, wherein the one movable piston is movable toward the first end of the first reactor unit during operation, and each of the third reactor units is provided with two movable pistons, wherein the two movable pistons are each moveable toward either end of the third reactor unit during operation.

19. The method of claim 18, wherein, the reactor system is configured to carry out the simulation experiment with no view zone and one well, by assembling in an order of first reactor unit, ball valve, mesh, second reactor unit, mesh, and cap, wherein the first reactor unit is configured to simulate a hydrate zone, the combination of ball valve, mesh, second reactor unit, and mesh is configured to simulate a sand control screen zone, and the cap is configured to simulate a sand production outlet;

wherein the reactor system being vertically assembled with the cap being disposed at bottom allows to carry out the simulation experiment with the sand control screens being disposed below the natural gas hydrate reservoir; or the reactor system being horizontally assembled allows to carry out the simulation experiment with the sand control screens being disposed laterally to the natural gas hydrate reservoir; or the reactor system being vertically assembled with the cap being disposed at top allows to carry out the simulation experiment with the sand control screens being disposed above the natural gas hydrate reservoir.

20. The method of claim 18, wherein, the reactor system is configured to carry out the simulation experiment with no view zone and two wells, by assembling in an order of cap, mesh, second reactor unit, mesh, ball valve, third reactor unit, ball valve, mesh, second reactor unit, mesh, and cap, wherein the third reactor unit is configured to simulate a hydrate zone, each combination of ball valve, mesh, second reactor unit, and mesh is configured to simulate a sand control screen zone, and each cap is configured to simulate a sand production outlet;

wherein the reactor system being vertically assembled allows to carry out the simulation experiment with the sand control screens being disposed above and below the natural gas hydrate reservoir; or the reactor system being horizontally assembled allows to carry out the simulation experiment with the sand control screens being disposed laterally to the natural gas hydrate reservoir.

* * * * *